United States Patent [19]
Foody et al.

[11] Patent Number: 5,970,805
[45] Date of Patent: Oct. 26, 1999

[54] FIBER SAMPLING DEVICE

[75] Inventors: Patrick J. Foody, Ottawa; Brian Creber, Dunrobin, both of Canada

[73] Assignee: Iogen Corporation, Ottawa, Canada

[21] Appl. No.: 09/027,721

[22] Filed: Feb. 23, 1998

[51] Int. Cl.[6] .................................................. G01N 1/00
[52] U.S. Cl. ....................................................... 73/863.85
[58] Field of Search ............................ 73/863.81, 863.85, 73/863.86; 162/263, 49

[56] References Cited

U.S. PATENT DOCUMENTS

| | | | |
|---|---|---|---|
| 2,615,339 | 10/1952 | Holgersson et al. . | |
| 4,220,499 | 9/1980 | Hughes, Jr. et al. . | |
| 5,366,592 | 11/1994 | Ford ...................................... | 73/863.86 |
| 5,370,146 | 12/1994 | King et al. ............................ | 73/863.86 |
| 5,585,576 | 12/1996 | Jaeger ................................... | 73/863.85 |
| 5,625,157 | 4/1997 | Piiraninen et al. ................... | 73/863.86 |

OTHER PUBLICATIONS

Kajaani SD–503 Sampling Device, Delivery Limits and Technical Specifications, Kajaani Electronics Ltd., (May, 1994).

ABB Process Automation, ABB Smart Pulping, Smart Pulp Platform, Asea Brown Boveri, Corporate Brochure (1993).

BTG Kappa Number Analyzer, Corporate Brochure (1995).

*Primary Examiner*—Robert Raevis
*Attorney, Agent, or Firm*—Fitzpatrick, Cella, Harper & Scinto

[57] ABSTRACT

A device for obtaining a sample of fiber from an aqueous slurry of fiber flowing through a stock line, comprising a first isolation inlet valve element together with a water supply orifice, located inside a fiber stock line; a second isolation valve means, and a third isolation valve, mounted in flow series from the sample inlet point on the stock line. This device allows a complete water purging down through the inlet valve element, as well as fiber samples to flow out of the stock line in the presence of diluent water. Samples flow from the first isolation valve means to a final collection point, without contamination or plugging.

10 Claims, 1 Drawing Sheet

FIBER SAMPLING DEVICE

BACKGROUND OF THE INVENTION

1. Field of the Invention

The present invention relates to an improved device for obtaining a sample of fiber from a fiber processing plant, such as a pulp or paper mill, a corn plant, or a starch plant. The improved fiber sampling device has several advantages over current sampling devices, including the ability to fully flush, in order to remove residual fiber, and the ability to be installed and removed while the plant is running. The improved fiber sampling device, therefore, allows fiber processing plants to obtain useful samples more easily and with less contamination than with current sampling units.

2. Brief Description of the Prior Art

A large number of industries are based on the processing of natural fiber. The pulp and paper industry, for example, converts wood fiber to pulp and paper products. The corn processing industry converts corn to starch, sugar, corn oil, and other products. Other crops, such as wheat and soybeans, are processed in an analogous manner. Cotton fiber is processed to make clothing and other textile goods.

One need that this wide range of industries has in common is the need for fiber sampling. All of the fiber processes are run at specified conditions (temperature, pH, salt concentration, etc.) and are run to a given degree of processing (chemical reaction, purity, removal of inhibitors, etc.). Although a good deal of automated instrumentation is available to monitor and control these process variables, in almost all plants there are some process variables that are not controlled automatically, and samples of the fiber are required for process control. In addition, most automated controls require occasional (or frequent) calibration with actual samples.

Much sampling of fiber is carried out manually. Manual fiber sampling consists of grabbing a sample of fiber with one's hands or with a scoop, where the fiber is openly exposed. If the fiber is flowing within a stock line, a manual sample can be taken by opening a valve attached to the line and using the pressure in the line to force the sample out. The sample is collected until the desired quantity is obtained, and the valve is then closed.

A more sophisticated form of manual sampling consists of two valves in series, connected by an intermediate pipe that is 6 to 12 inches long. The valve closer to the stock line, hereinafter referred to as the first isolation valve, is opened and closed to take a sample; the valve farther from the stock line, hereinafter referred to as the second isolation valve, is closed except when removing a sample from the pipe. To take a sample, the first valve is opened to fill the intermediate pipe with fiber. The first valve is then closed, and the second valve is opened to allow removal of the fiber sample.

An advantageous variant of the two-valves in series is to add a third valve to the system, which is attached to a T coming off the intermediate pipe. This third valve can be opened to allow water into the intermediate pipe, and force the fiber sample out when the second isolation valve is open.

Such a known three-valve sampler can be installed on-line, that is, while the plant is running, and fiber is flowing through the stock line under pressure. This is advantageous, as it avoids the need to shut down the mill to install the sampler. On-line installation is carried out using a so-called hot-tap procedure. A first valve is connected to one end of a pipe nipple, the other end of the nipple then is welded to a stock line. A hot tap apparatus is attached to the other part of the first valve. The valve is opened; a drill bit is pushed through the opening within the valve body; until it bores through the wall of the stock line. The drill bit then is removed through the valve body and the first valve is closed. A first valve so attached to the stock line then is ready to be attached to an intermediate pipe and a second valve.

There are several disadvantages associated with known three valve systems. First, there is no water flush between the first valve and the stock line, and fiber can build up at this point, and contaminate subsequent samples. Second, there is no technique to remove the entire system on-line, for cleaning or maintenance.

While operation of known three valve samples can be automated, so as to allow the samples to be taken automatically, such automation does not overcome the inherent disadvantages of the unit during automatic sampling.

For frequent or multiple samples, and for situations where a sample must be moved a large distance for analysis, certain automated sampling units are known. Several known commercial sampling devices are listed in Table 1. These devices are used for specific solids consistencies, pipe diameters, process temperatures, and materials of construction. In each device a sample is conveyed to a desired location or instrument by either:

1. Internal pressure in the stock line, which feeds the sample directly to the instrument a short distance away.

2. A piston-type pressure, where a moving piston conveys a sample of fiber a distance of 50–200 feet.

3. A flowing-type, where water conveys the sample to the instrument.

A typical example of such devices, is the Kajaani SD-503, which contains a sampling valve element that is inserted into the stock line, and is electrically actuated from outside the stock line. The tip of the sampling valve is a plunger that opens and closes to admit a sample. This sampling valve is short (with a length less than two inches), and has an inlet port coupled to the stock line by a process coupling. The outlet part of the sampling valve is attached to a sample chamber. The pulp samples pass through a sample chamber and out of a hose, to a remote location. Water is admitted to the sampling chamber, at a point just downstream from the process coupling. This water is used to convey the samples out of the sample chamber, and into the hose.

One shortcoming of the SD-503 sampling device is the inability to do a complete water flushing of the sample chamber. The system is not designed for flush water to penetrate all the way to the sampling valve element. In addition, crevices within the sample chamber catch and hold fiber. This makes fiber buildup at or near the isolation valve likely, which causes cross contamination of samples. Another shortcoming of the SD-503 sampling device is that it cannot be installed or removed on-line. The requirement to shut down the plant or fiber line before installing or removing the sampling valve element is a serious inconvenience, and cost factor.

TABLE 1

AUTOMATIC SAMPLING DEVICES

| MANU-FACTURER | UNIT | SOLIDS CONSISTENCY | PIPE DIAMETER | SPECIAL FEATURES |
|---|---|---|---|---|
| ABB | 1000 | <6% | not specified | EPDM seal |
|  | 1001 | <6% | not specified | Viton seal |
|  | 1002 | <6% | not specified | Screens sample |
|  | 1003 | 6–14% | not specified | EPDM seal |
|  | 1004 | 6–14% | not specified | Screens pulp |
|  | MCB-1003 | 6–14% | not specified | Screens pulp |
| BTG | HDS-1010 | >12% | not specified | temp >150 C. |
|  | HDS-1100 | >12% | not specified | temp >150 C. |
|  | MDS-1100 | 5–12% | not specified |  |
|  | LDS-1100 | <5% | not specified |  |
| KAJAANI | SD-501 | 6–15% | not specified | piston type |
|  | SD-502 | 0.5–6% | <8 inches | flow type |
|  | SD-503 | 0.5–6% | <4 inches | titanium |

Therefore, in spite of the availability of a wide variety of fiber samplers, there are significant shortcomings with such known devices. Those shortcomings are addressed by the present invention.

SUMMARY OF THE INVENTION

The inventor has developed a device for sampling fiber automatically that can be completely flushed to avoid fiber buildup, and that also can be installed and removed on-line. The invention enables operators of fiber processing plants to obtain samples more conveniently and without cross-contamination from previous samples. Hence, the present invention results in better quality samples, with less effort and lower maintenance. A unique aspect of the fiber sampler taught herein is a first isolation valve and sample chamber with a water flushing configuration that enables both to be completely flushed with water, thereby eliminating cross contamination of fiber samples. In a preferred embodiment, the fiber sampler valve element can be inserted through a valve and into a stock line for on-line installation and removal.

BRIEF DESCRIPTION OF THE DRAWING

The invention is illustrated in a preferred embodiment by reference to the accompanying drawing in which.

DETAILED DESCRIPTION OF A PREFERRED EMBODIMENT

Figure 1:
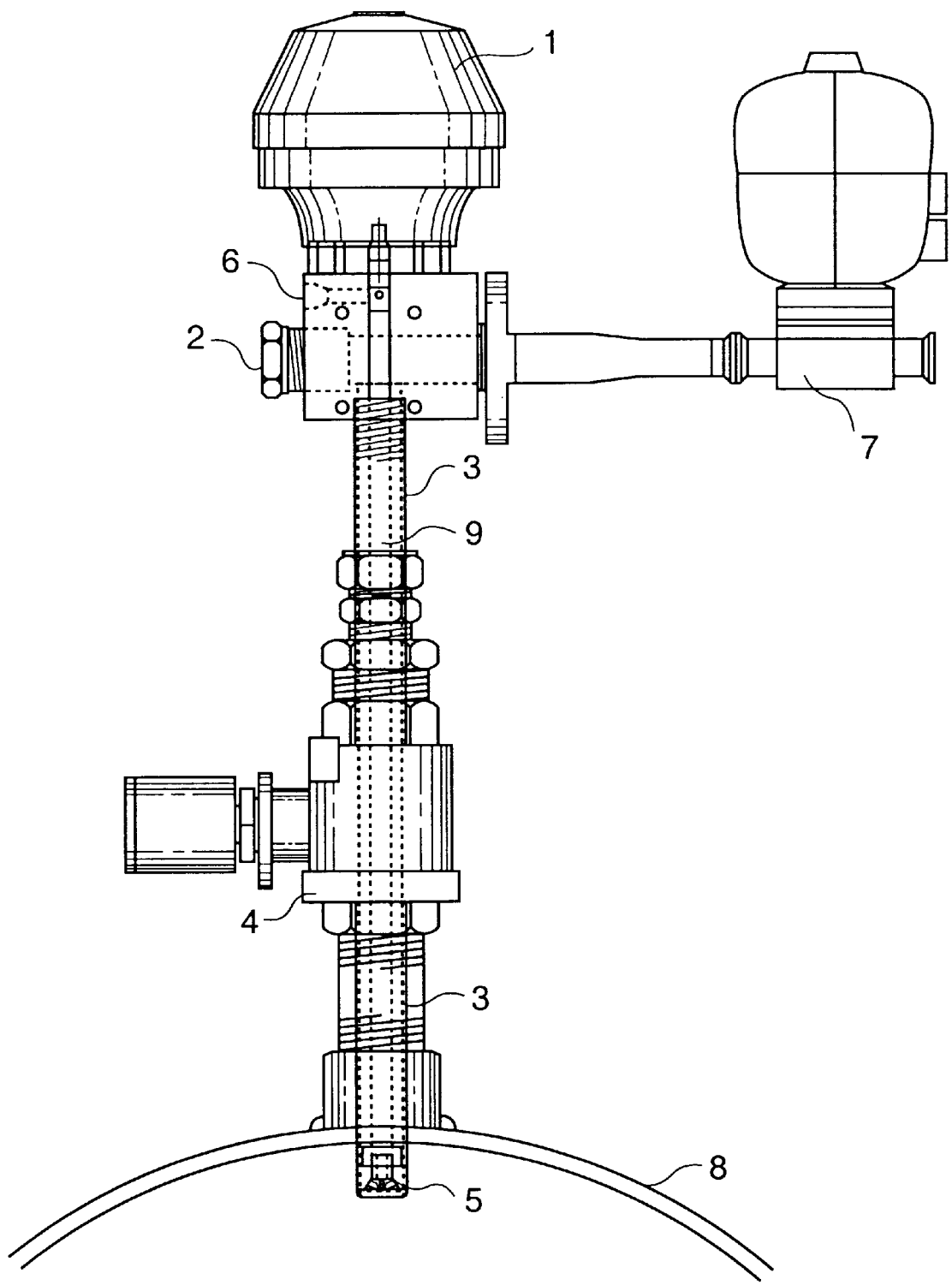
FIG. 1 is a schematic vertical elevation view of a preferred embodiment of an automated sampling device according to the present invention.

FIG. 1 illustrates a preferred embodiment in use, wherein an automated sampling device has been mounted upon a fiber stock line. The device essentially comprises a fiber sampler valve element 5 located within the stock line, and controlled by a linear actuator 1. Valve 5 is the first, or primary isolation means controlling the flow of fiber within and out the sampler. The actuator 1 is a pneumatic solenoid that acts linearly upon the first, or sampler valve element 5 through a hollow tube 9, in order to open and close valve element 5 against a conical or spherical seat, in the fashion of a tappet valve. A second, or secondary isolation valve in this embodiment preferably is a ball valve 4, through which an entire tubular sample chamber 3 may be inserted. Valve 4 is open unless the sampler is being removed. This embodiment also includes a third, or tertiary remote isolation valve 7, as well as liquid inlet ports 2 and 6, to regulate the flow of water into the system. Liquid port 2 is connected to a high pressure water main line, by a conventional valve (not shown).

A sampling cycle may starts with an initial fiber purge, wherein valve 7 is closed and actuator 1 through hollow tube 9 opens the sampler valve element 5. Water or other cleaning liquid can be forced through inlet ports 2 and 6, to respectively flow outside and inside the hollow tube 9, through openings located at the base of hollow tube 9 down past sampler valve element 5 and into stock line 8. This flushing configuration passes water through the entire sample chamber 3, both inside and outside actuator tube 9, within tubular chamber 3. The chamber and tube geometry illustrated in FIG. 1 is defined by smooth and clear surfaces, to eliminate any sharp crevices where fiber will accumulate. By this, or another type of flushing actions, as described hereafter, there is a purge which completely removes residual fiber from the sampler device, thereby preventing contamination of subsequent samples.

When an initial fiber purge is complete, actuator 1 is set to leave sampler valve element 5 opened; third isolation valve 7 is opened; and the water source into liquid inlet port 2 is closed, so as to depressurize entire the sampler. Internal pressure inside stock line 8 forces stock fiber through valve element 5 and into tubular sample chamber 3, and specifically into an annulus defined outside actuator tube 9. The fiber sample then is transported up tube 3 towards third isolation valve 7.

When sufficient fiber sample is collected, the actuator 1 closes first valve element 5, and high pressure water from a main water line, is admitted at liquid inlet port 2. The sample then is transported downstream past third valve 7, by water flowing from inlet port 2.

A reverse, or backflushing, type of initial purge may not always be needed. When sufficient fiber has been collected, diluent water from inlet port 6 can simultaneously be forced to flow down tube 9 towards closed valve element 5, through openings located at the base of actuator tube 9 in close proximity to valve element 5, and then back up the outside annulus of tube 9. This action then will act as an important, second purge in order to remove stray fiber from the sample chamber. When a sample reaches its destination, and both valve 5 and the third isolation valve 7 are closed, then water pressure inside sample chamber 3 can be allowed to rise above the internal pressure in the stock line 8, and be in readiness for another initial purge. A cycling of valves 1 and 7 to so adjust pressure inside the sample chamber 3 can be controlled conventionally by an external timer circuit or computer (not shown), in a conventional manner.

A stock sample first is diluted with water, at or near to the sample valve element 5 through openings located at the base of actuator tube 9. Diluent water can be added through inlet port 2, from a high pressure, main water line, while a sample is being taken from the stock line. In a most preferred embodiment, as illustrated in FIG. 1, the stock is diluted with water entering inlet port 6, from a low pressure water line, with diluent water traveling inside and down actuator tube 9, and is admitted to the stock sample at or near valve element 5. A typical dilution (expressed as weight water: weight stock) is about 10:1, but this ratio can be varied widely by pulsing the dilution water source or varying the dilution water pressure relative to the stock pressure. Such controlled dilution at the sample valve element advantageously allows sampling of slurries with higher fiber consistency. Existing automatic sampling devices that use water to convey a fiber sample do not dilute the sample at the initial point of sampling, but rather at an instrument or other remote location. Such remote dilution increases the possibility of plugging the sample line near the stock line.

Installation of a secondary isolation valve 4 can be carried out on-line using a hot-tap procedure, as described above. Once ball-type valve element inside valve 4 is opened, a distal end of tubular chamber 3 and tube 9 (with valve element 5) is inserted downwardly therethrough, and the proximate end of the tube is connected directly to a linear actuator connector on the solenoid actuator 1. The sampler unit is then operated with ball valve 4 always open.

The sampler assembly is removed from the stock line, for cleaning or maintenance, by raising the distal end of tubular chamber 3 and tube 9 up through secondary isolation valve 4, and then closing that valve. Then the upper assembly is removed from the threaded nipple connection shown just above valve 4. This does not disrupt the flow or pressure in the stock line.

For best operation, the cylindrical opening in the ball valve element of secondary isolation valve 4 maintains a leak-tight seal against the outside of the tubular sample chamber 3. This arrangement is self-centering and self-correcting for any wear or damage due to sand inside the fiber line.

In essence, the tubular sample chamber 3 is designed to allow the water flush to completely remove fiber from inside that chamber. This is accomplished by allowing the water flush an unimpeded flow out of the chamber, and locating the flow such that it is unidirectional and not encumbered with twists, turns, stagnant zones, or other configurations that catch or hold fiber or result in incomplete fiber removal. In the embodiment illustrated by FIG. 1, the sample chamber consists of the annulus between concentric, cylindrical tubes, with tube 9 an inner cylinder and chamber 3 an outer cylinder. The water flush is carried out by flowing water out of both tube 9 and the annulus outside tube 9. There is no other space within the sample chamber for fiber to accumulate.

It will be recognized by those skilled in the art that several alternate designs are possible, including but not limited to the inner cylinder located off-center to the outer cylinder, or the presence of more than one inner cylinder, or conduits of non-cylindrical shapes.

In the preferred embodiment, the fiber sample flows in the annulus between the coaxial cylinders. It will be recognized by those skilled in the art that several alternate designs are possible, including fiber flowing within the inner cylinder.

In the preferred embodiment of FIG. 1, the entire sample chamber is inserted slidably within a cylindrical passage in a ball valve element. This allows the chamber to be installed or removed on-line. The minimum length of such a sample chamber (3) to insert through a valve and protrude into the stock line is about 4 inches. A preferred length is about 8 to 18 inches. Sample chambers longer than this length are difficult to flush completely. The maximum practical size of chamber 3 at the point which passes through the ball valve 4 is an outer diameter of about 1.5 inches. If the diameter is larger than this, the force required to manually install and remove the device, which must overcome the pressure force of the stock line, is too great. A more preferred outer diameter of the sample chamber is less than about 0.75 inches.

Primary isolation valve means (5) can in practice be any means of isolating the fiber sample from the stock line and opening and closing to admit samples. Several embodiments familiar to those skilled in the art are conical seat valves, flanges, diaphragms, and couplings.

The primary isolation valve means can be actuated by a pneumatic actuator, an electric actuator, or other device familiar to those skilled in the art. The actuator is located outside of the fiber source, in contrast to valve 5, which is located within the fiber source. In the preferred embodiment shown in FIG. 1, valve element 5 is actuated pneumatically. In the preferred embodiment, actuator 1 is a pneumatic solenoid.

The secondary isolation valve means can be any valve or similar device familiar to those skilled in the art, that permits the passage of a tube 3 through a valve opening. Some examples of this are ball valves, gate valves, butterfly valves, and diaphragm valves. In a preferred embodiment, a ball valve is used, wherein the opening of the valve is straight to allow the insertion of the main sampler tube. In a preferred embodiment, the valve also has threaded inlet and outlet ports. In a most preferred embodiment shown in FIG. 1, the valve 4 is a threaded ball valve.

The tertiary isolation valve means can be any valve or similar device familiar to those skilled in the art, which permits the passage of fiber slurry when opened, including a ball valve, gate valve, diaphragm valve, butterfly valve, or other valve device. In a preferred embodiment shown in FIG. 1, a sanitary diaphragm valve is used to allow for rapid opening and closing.

Transport water inlet means, connected to high pressure water, can employ any valve or similar device familiar to those skilled in the art, that is used to control the flow of water. In a preferred embodiment, liquid inlet port 2 includes a nearby solenoid valve. In a most preferred embodiment shown in FIG. 1, a valve proximate inlet 2 is a solenoid diaphragm valve.

Diluent water inlet means, connected to a smaller water line, can employ any valve or similar device familiar to those skilled in the art, that is used to control the flow of water. In a preferred embodiment, liquid inlet port 6 includes a nearby solenoid valve. In a most preferred embodiment shown in FIG. 1, a valve proximate inlet 6 is electric solenoid diaphragm valve.

The fiber sampler parts can be manufactured using stainless steel, other metals, or plastics compatible with the chemicals present in the materials being sampled. In a preferred embodiment, the body of fiber sampler is made using titanium.

While the embodiment illustrated in FIG. 1 shows the sampler mounted to a source of fiber that is a fiber stock line, any pressurized containment, such as a surge tank, is equivalent to the illustrated section of stock line. In practice, the sampler can be mounted to any aqueous fiber slurry containment that is under at least 0.5 psig pressure, to force the sample into the sampler unit. Such containments include but are not limited to hold tanks, surge tanks, and stock lines.

While a preferred embodiment has been shown and described, the invention is to defined solely by the scope of the appended claims.

I claim:

1. A device for obtaining a fiber sample from an aqueous slurry of fiber within a pressurized containment, comprising in combination and mounted in flow series downstream from an inlet point on said containment:

a first isolation valve means proximate to the inlet point from said containment;

a sample chamber comprising an inner and outer portion;

a second isolation valve means;

at least one water introduction means, whereby a sample flowing out of said containment can be mixed, purged or both mixed and purged with water at said inlet point; and a third isolation means, wherein said sample chamber is removable from said containment without disrupting flow within said containment.

2. The device of claim 1 wherein said pressurized containment is a stock line; said first isolation valve means further comprises a remote linear actuator that is connected to a first valve element that is within said stock line; said connection further comprising an actuator tube having a proximate end that is connected to said remote linear actuator and a distal end that supports said first valve element, wherein said actuator tube extends through said second isolation valve means.

3. The device of claim 2 wherein the water introduction means further comprises a source of diluent water that selectively is delivered to a sample, at a point proximate to the first valve element, by said actuator tube located inside said sample chamber, said outer portion of said sample chamber being tubular and fitting slidably through an opened ball valve element, which comprises said second isolation valve means.

4. The device of claim 3 wherein the outer diameter of the tubular sample chamber is less than 1.5 inches.

5. The device of claim 1, wherein at least one water introduction means further comprises said sample chamber connected to at least one source of purging water that is capable of flushing remains of said fiber sample in said sample chamber either out past the first isolation valve means and into said containment, or out past said third valve means.

6. The device of claim 5 wherein the at least one source of purging water is introduced into an end of said sample chamber that is proximate to said third isolation valve, said purging water flushing out said outer portion of said sample chamber located between the outside of an actuator tube and the inside of a surrounding cylindrical tube.

7. The device of claim 6 wherein the actuator tube and surrounding cylindrical tube are substantially concentric, and pulp fiber is transported in an annulus defined between the actuator tube and the cylindrical tube.

8. The device of claim 6 wherein the water introduction means further comprises a source of diluent water that is transported by said actuator tube to an orifice that is proximate to said first valve means.

9. The device of claim 5 wherein said fiber sample enters said outer portion of said sample chamber defined between the outside of an actuator tube and the inside of a surrounding cylindrical tube.

10. The device of claim 5 wherein at least one water introduction means further comprises a source of diluent water that is transported by said inner portion of said sample chamber to an orifice that is proximate to said first isolation valve means.

* * * * *